(12) United States Patent
Pitkänen et al.

(10) Patent No.: US 8,329,476 B2
(45) Date of Patent: Dec. 11, 2012

(54) SAMPLE PORT, MULTI-LAYER FILTER, SAMPLING METHOD, AND USE OF A SAMPLE PORT IN SAMPLING

(75) Inventors: Juha-Pekka Pitkänen, VTT (FI); Ari Hokkanen, VTT (FI); Päivi Heimala, VTT (FI); Jari Kauhaniemi, Raisio (FI); Kai Kolari, VTT (FI); Pekka Savolahti, VTT (FI); Jaana Uusitalo, VTT (FI)

(73) Assignee: Teknologian Tutkimuskeskus VTT, VTT (FI)

( * ) Notice: Subject to any disclaimer, the term of this patent is extended or adjusted under 35 U.S.C. 154(b) by 0 days.

(21) Appl. No.: 13/321,804

(22) PCT Filed: May 21, 2010

(86) PCT No.: PCT/FI2010/050410
§ 371 (c)(1),
(2), (4) Date: Jan. 20, 2012

(87) PCT Pub. No.: WO2010/133771
PCT Pub. Date: Nov. 25, 2010

(65) Prior Publication Data
US 2012/0115243 A1 May 10, 2012

(30) Foreign Application Priority Data

May 22, 2009 (FI) .................................. 20095568

(51) Int. Cl.
*G01N 1/18* (2006.01)
*B01D 35/00* (2006.01)
(52) U.S. Cl. ........ 436/177; 436/174; 436/178; 436/180; 422/513; 422/527; 422/534

(58) Field of Classification Search .................. 436/174, 436/177, 178, 180; 422/68.1, 501, 513, 527, 422/534, 535; 435/283.1, 287.1, 288.6
See application file for complete search history.

(56) References Cited

U.S. PATENT DOCUMENTS

| 4,269,064 | A |   | 5/1981  | Johnson et al.         |
|-----------|---|---|---------|------------------------|
| 4,475,410 | A |   | 10/1984 | Jaeger                 |
| 4,487,696 | A |   | 12/1984 | Ferrara                |
| 4,597,868 | A | * | 7/1986  | Watanabe ....... 210/232 |

(Continued)

FOREIGN PATENT DOCUMENTS
EP 0192361 A2 8/1986
(Continued)

*Primary Examiner* — Maureen Wallenhorst
(74) *Attorney, Agent, or Firm* — Birch, Stewart, Kolasch & Birch, LLP

(57) ABSTRACT

A sample port includes a body equipped with an internal cavity and two plungers arranged moveably in the internal cavity, whereby the plungers can be pressed against each other in the internal cavity, in order to compress a sample. At least one of the plungers can be moved into a reactor in order to collect a sample. The sample port also includes a sample chamber, which is formed by a space remaining between the internal cavity and the plungers. At least one sample-container connection is connected in connection with the internal cavity in order to collect the sample from sample chamber. In addition, the sample port has a filter which is provided to at least either plunger for separating a liquid component of the sample from a solid component and means for leading the liquid component of the sample out of the sample chamber.

31 Claims, 13 Drawing Sheets

U.S. PATENT DOCUMENTS

Figure 1:
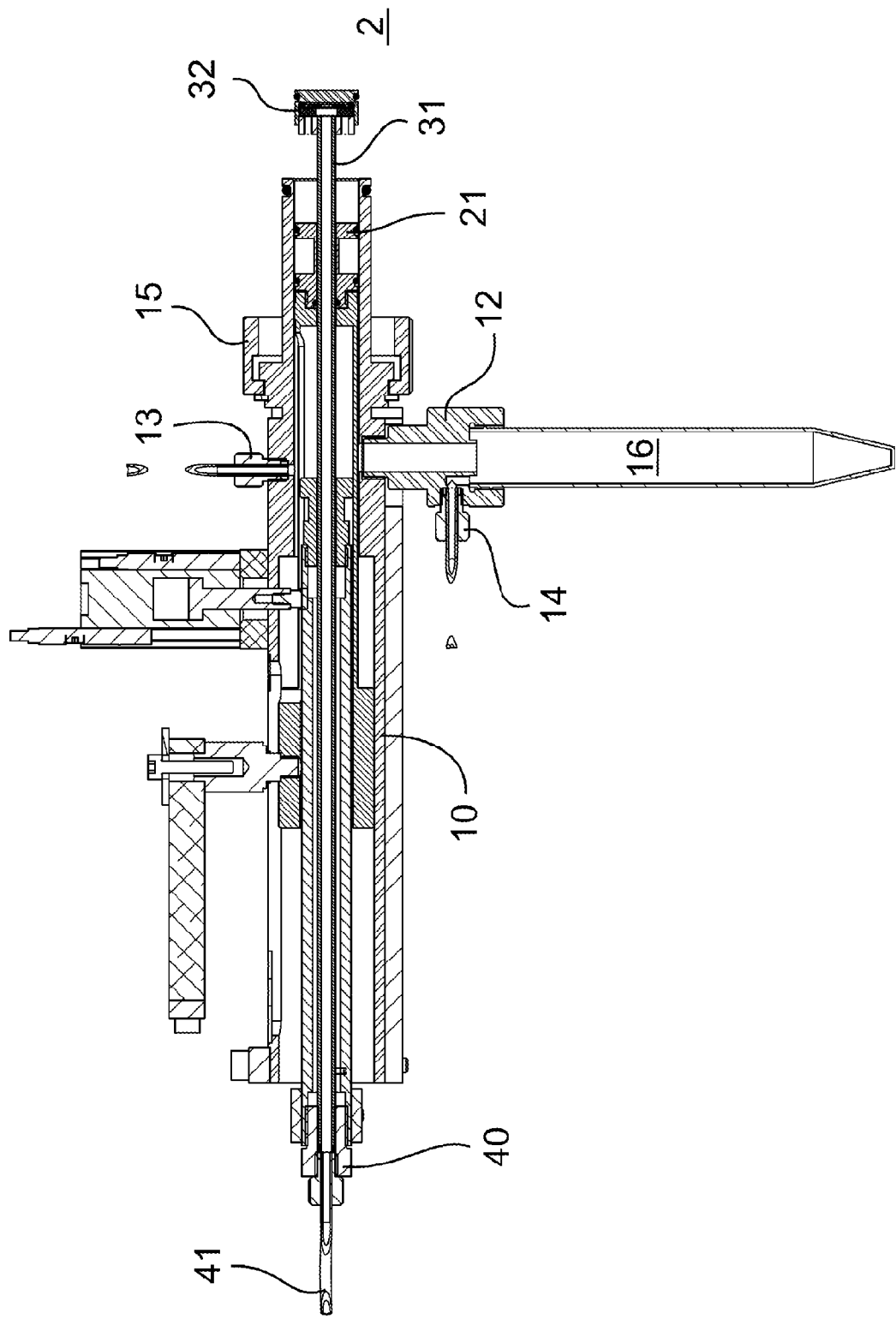

| | | |
|---|---|---|
| 4,744,255 A | 5/1988 | Jaeger |
| 2007/0144274 A1 | 6/2007 | Gibson et al. |
| 2007/0272038 A1 | 11/2007 | Schadt |
| 2008/0302829 A1* | 12/2008 | Smernoff ................. 222/189.09 |

FOREIGN PATENT DOCUMENTS

| | | |
|---|---|---|
| EP | 0325910 A1 | 8/1989 |
| EP | 0724145 B1 | 3/2004 |

* cited by examiner

SAMPLE PORT, MULTI-LAYER FILTER, SAMPLING METHOD, AND USE OF A SAMPLE PORT IN SAMPLING

The present invention relates to the processing of a sample and especially to the separating of a liquid and solid sample component in connection with sampling and the recovery of different sample components. The invention relates particularly to sampling from a bioreactor growth, in which there is a high solids content, or a high viscosity. More specifically, the invention relates to a sample port, a multi-layer filter, a sampling method, and the use of a sample fate in sampling, as well as the separation of a solid and liquid sample component in connection with sampling, according to the preambles to claims 1, 15 and 21 respectively.

From the point of view of the effective control of bioprocesses and processes in general, it is important to be able to monitor critical process parameters. Samples for analysis must therefore often be taken from a reaction vessel. Particularly in processes with a high solids content, which are increasingly being aimed at, sampling is very much a current challenge, for which some solutions are known. A substance can be recovered either manually, or using an automated recovery device, known as a sample port, connected directly to the bioreactor. In such cases, sampling will not succeed using conventional piping and taps based solely on a difference in pressure, due to the poor flow properties of the pulpy or nearly solid substance with a high solids content, or a high viscosity. Therefore, several different solutions, suitable for processes with a high solids content, have been developed, such as conveyors, such as screw conveyors, conveying the substance out of the reactor. However, the use of screw conveyors in sampling is not optimal, as only a small fraction of the sample removed from the reactor can be utilized. The rest remains unnecessarily as waste in the conveyor space between the reactor and the sampling container.

To achieve a higher efficiency, lossless sampling methods and devices have been developed, in which the surplus sample is transported back to the reactor. Such devices are usually extremely complex and are not suitable for applications demanding reliability. This is because, when recycling the sample back, there is the danger that external organisms contaminating the growth will also be transported back. Thus, the sampling is not aseptic. In addition, sampling methods are known, according to which a sample in the form of a solution is filtered in situ through sinter or a filter membrane. However, the collection systems described become blocked very quickly and impurities collected on the filter cannot be removed during the growth of the substance being studied. A solution is also known for recovering pulpy substances from a reactor, in which solution a plunger is arranged to push into the reactor and, on the return stroke, to push the sample in front of it into a sample port. The sample is compressed inside the sample port, in order to eject it into a sample container below the port. An example of such a device is the Isolok Series MSD sampler, in the hollow body of which is a counter plunger, against which the plunger pushing into the reactor compresses the pulpy sample, after which the sample is collected. The device in question, and the manufacturer's other devices do not permit the separation of a dissolved sample component from a solid sample component immediately during sampling. In addition, cleaning and sterilization of the devices in question between samplings is challenging, or, if automated, even impossible.

However, other significant drawbacks are associated with the known solutions. Solutions based on conveyors, such as screw conveyors, are inefficient, as they waste samples or require a separate return delivery system for the sample, which increases both the complexity of the device and its risk of contamination from external organisms. Even the known techniques that do not waste substances are mainly suitable only for liquid samples. On the other hand, systems based on filters are also inefficient, on account of the said cleaning problems. However, the most significant problem common to the known solutions is that a liquid sample component cannot be repeatedly and automatically filtered out of a sample containing a high solids content. This is because the liquid and solid phase of the sample must often be separated for the automated analysis following the sampling. At present pulpy samples must be processed separately after sampling, in order to separate the liquid component, which is disadvantageous due to the additional labour-intensive work stage, and thus does not permit the process to be adjusted rapidly and automatically based on the measurement results.

The invention is intended to eliminate at least some of the drawbacks of the prior art and create a sample port, with the aid of which a sample, which has a high solids content, can be collected automatically from a bioreactor growth, in such a way that the sample is not wasted and that a liquid and dry sample component can be separated form the sample in the same connection.

The aims of the invention are achieved using a sample port, filter, or sampling method like those described hereinafter.

The sample port according to the invention comprises a body equipped with an internal cavity and two plungers arranged to move in this, which can be pressed against each other in order to pressurize a sample in the internal cavity, at least one of which plungers can be moved in order to collect a sample. The sample port also comprises a sample chamber, which is formed in the space remaining between the internal cavity and the plungers, and at least one sample-container connection, which is connected to the internal cavity, in order to collect a sample from the sample chamber. In addition, the sample port has filter means adapted to at least either plunger for separating the liquid component of a sample from its solid component, and means for leading the liquid component of the sample out of the sample chamber.

More specifically, the sample port according to the invention is characterized by what is stated in the characterizing portion of claim 1.

The multi-layer filter according to the invention, for the sample port according to the invention, comprises a body, which is equipped with a through hole, as well as a number of filter elements, which are fitted to the body around this through hole, each of which comprising at least one filtering membrane, which is equipped with holes according to the filtering requirement.

More specifically, the filter according to the invention is characterized by what is stated in the characterizing portion of claim 15.

In the sampling method according to the invention, the first plunger is pushed into the bioreactor or similar, and the first plunger is retracted into the hollow body of the sample port, so that the plunger pushes the sample in front of it. The sample is compressed between the second plunger and the first plunger, so that the liquid phase of the sample is filtered by pressing the sample through the filter of the first plunger, and is led into the sample connection through the hollow rod of the first plunger. Finally, the solid phase of the sample is ejected into the sample-container connection.

More specifically, the sampling method according to the invention is characterized by what is stated in the characterizing portion of claim 21.

Considerable advantages are gained with the aid of the invention. This is because, by means of the sample port according to the invention, samples, which have a high solids contact, can be taken automatically from bioreactors and similar, in such a way that the sample can be collected without waste sample, as well as separately in a liquid and a solid phase. After sampling, the sample port can be automatically cleaned and sterilized. The sample port according to the invention can also be used for processes other than those with a high solids content, such as for more conventional, freely flowing, bioreactor growths with a lower viscosity. Thanks to the in situ sampling, which is rapid, reliable and can be automated, the sample port according to the invention can be used to achieve online measurement results, based on which the process can be adjusted in nearly real time.

According to one embodiment, the sample is preferably filtered through a multi-layer filter plate made from silicon, which filter comprises very small holes to prevent the passage of microbial cells. Thanks to its multi stages and the orientation of the holes, the filter plate offers easier cleaning than porous ceramic filters, which is important to ensure continuous, repeatable, and automatic operation.

According to one embodiment, sample ports according to the invention are connected in series, in such a way that the solid-sample sample-container connection of the first sample port is connected together with the sample chamber of the second sample port, which achieves the advantage that a solid sample component can be extracted automatically for subsequent automatic analysis. Automatic extraction permits automatic analysis, which permits automatic control of the process, which permits greater productivity of the process.

Figure 2:
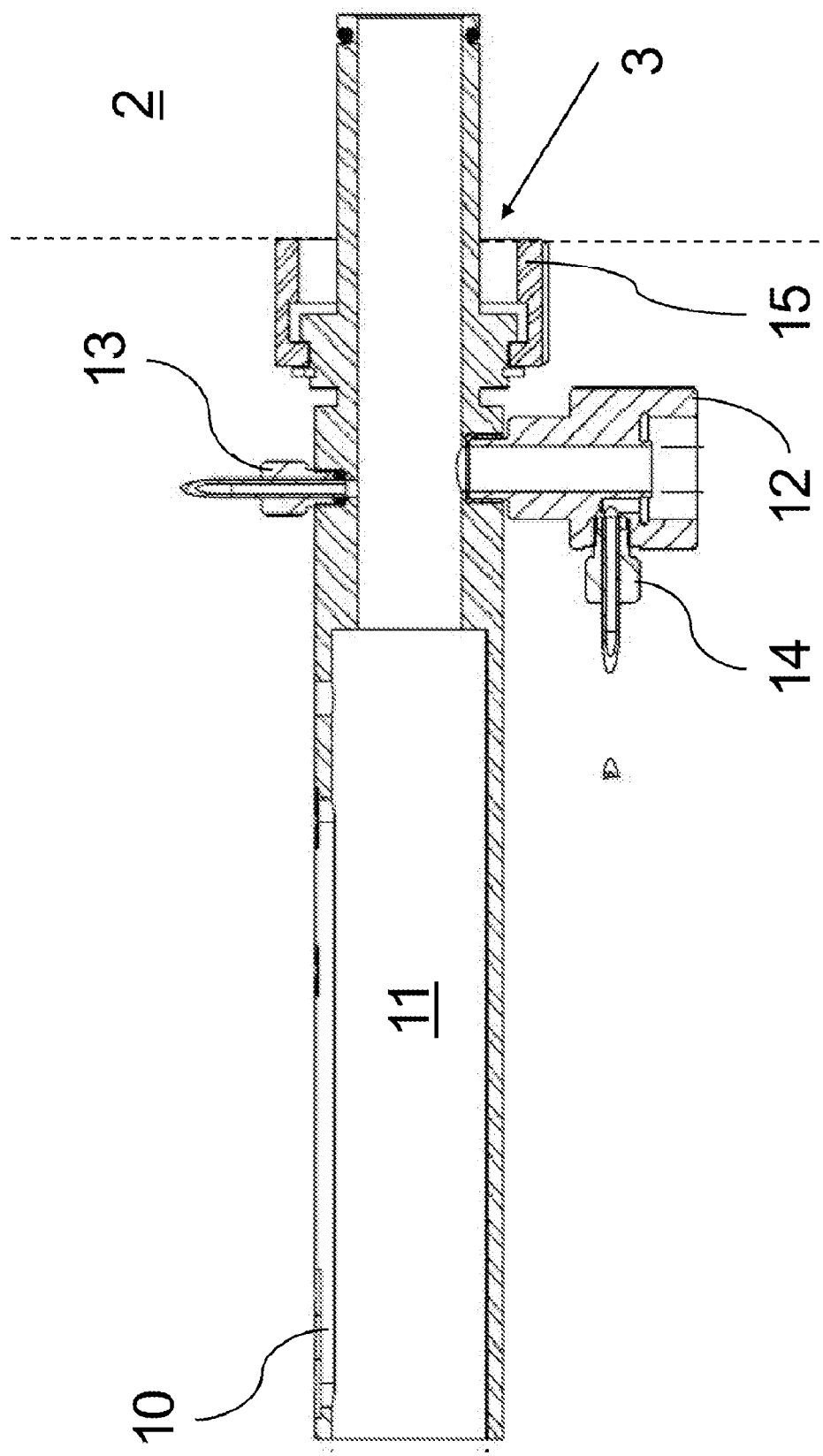
Figure 3:
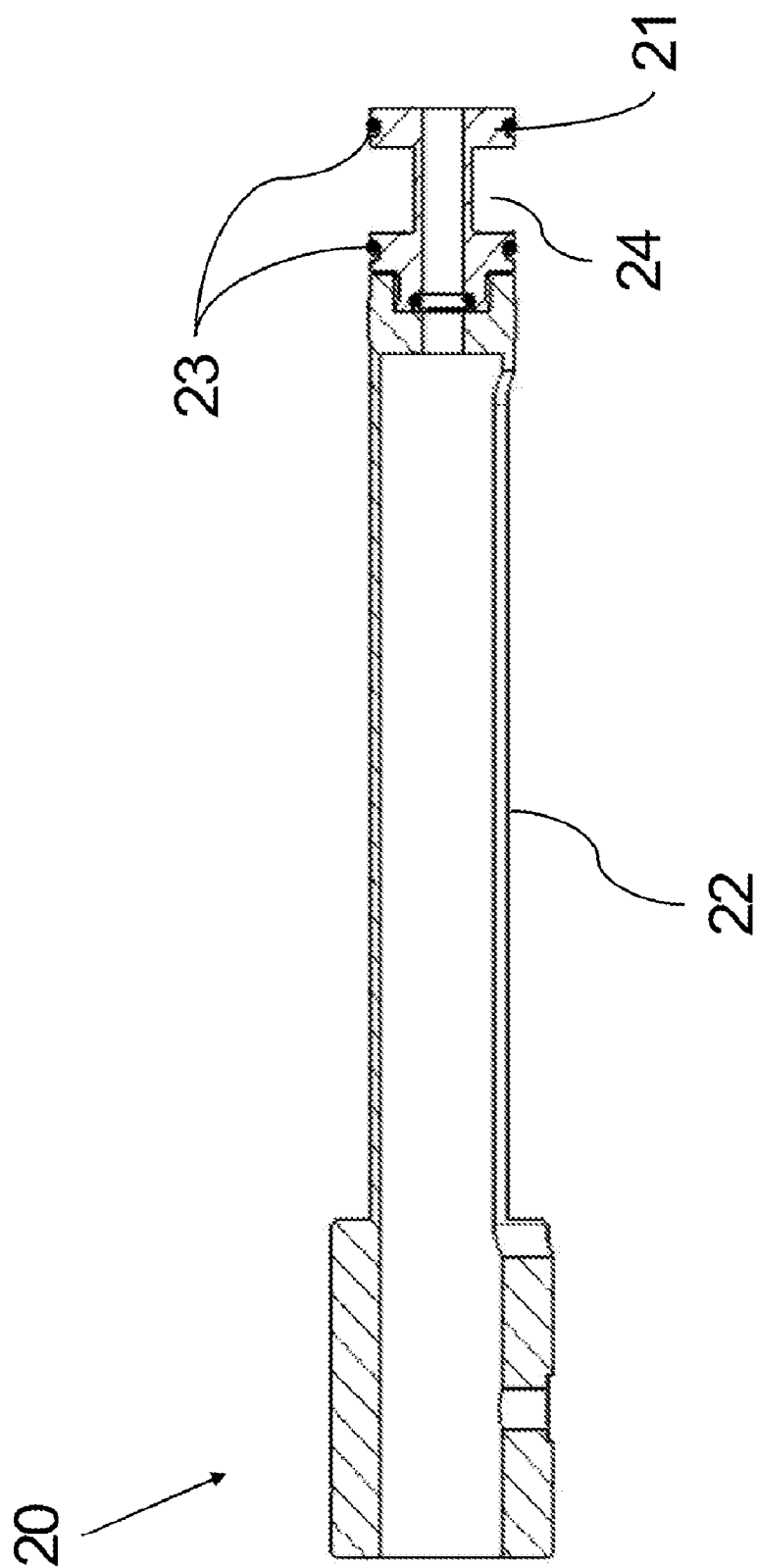
Figure 4:
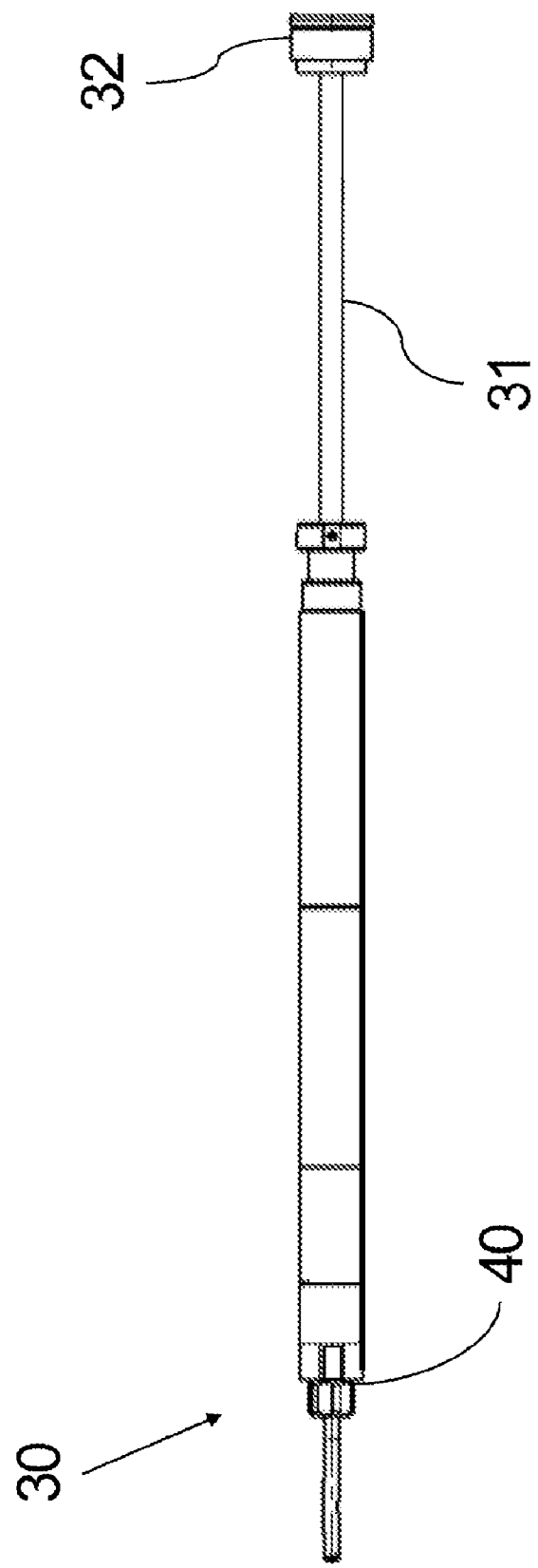
Figure 5:
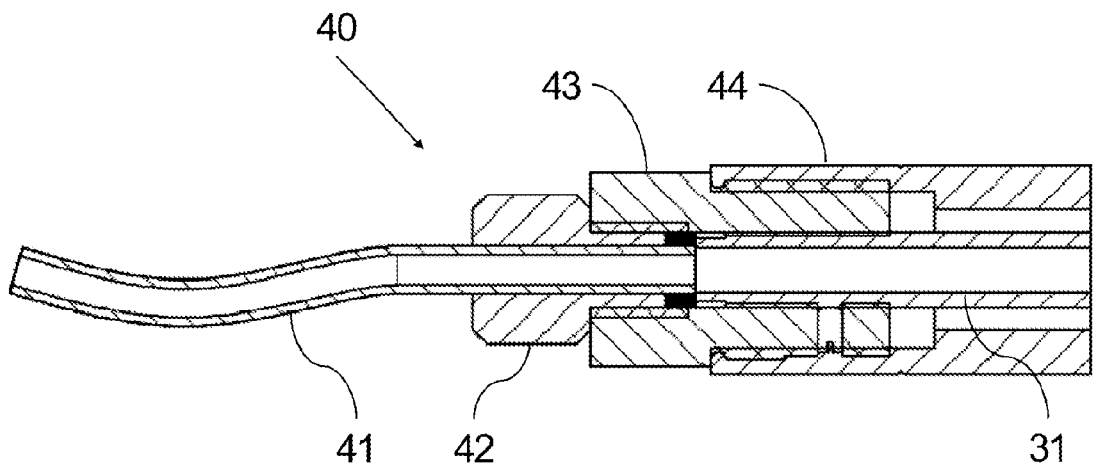
Figure 6:
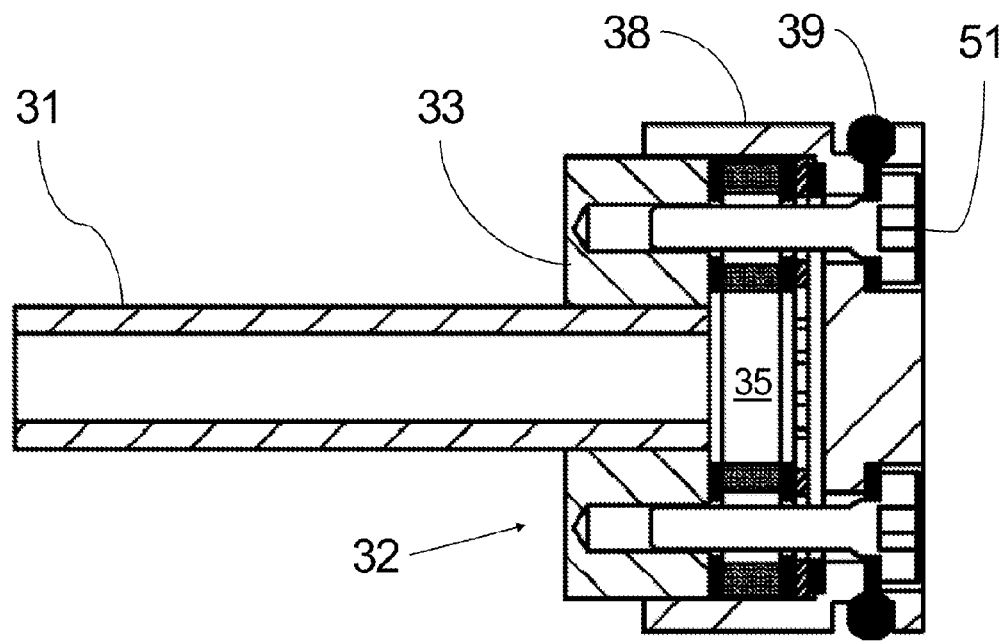
Figure 7:
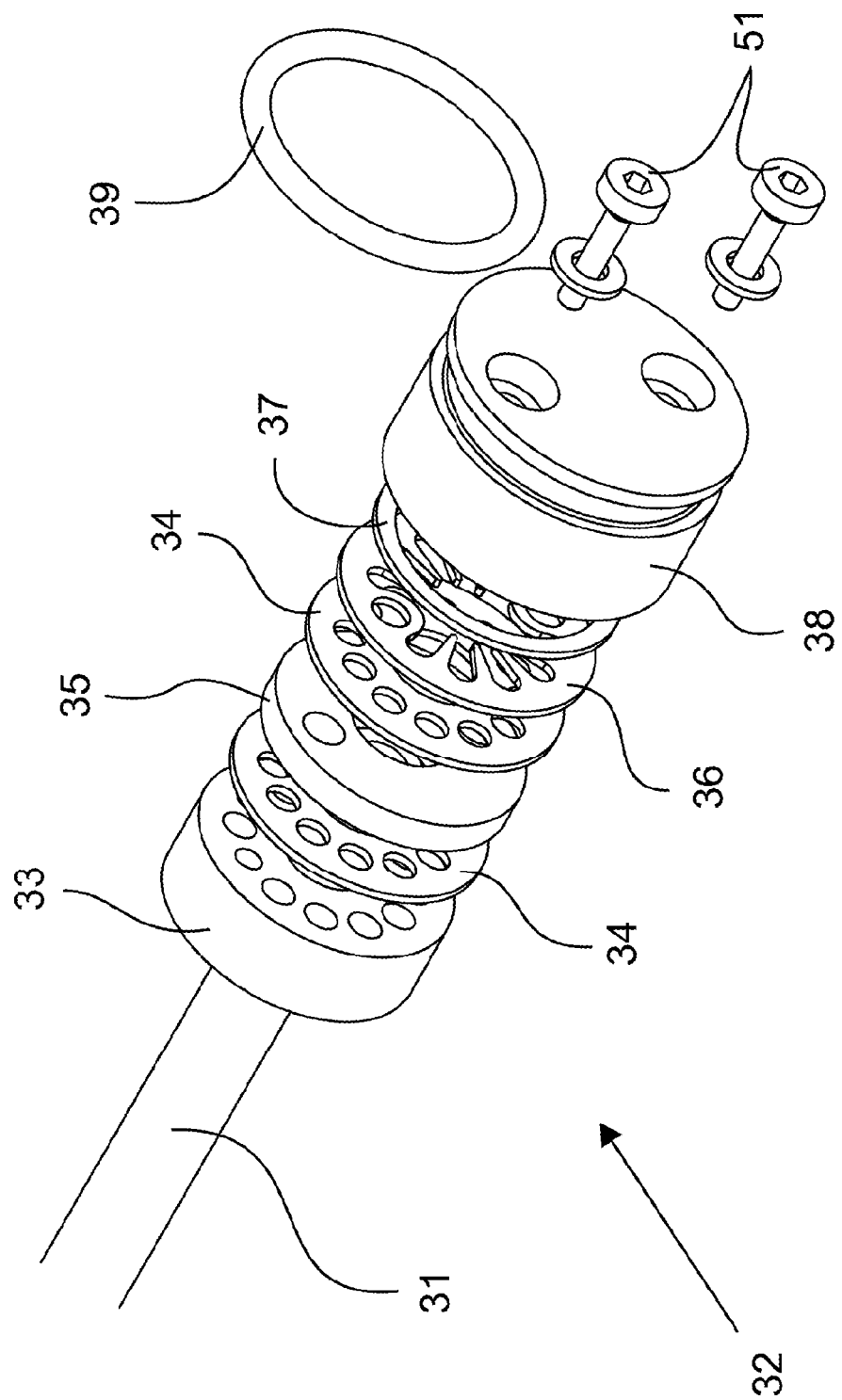
Figure 8:
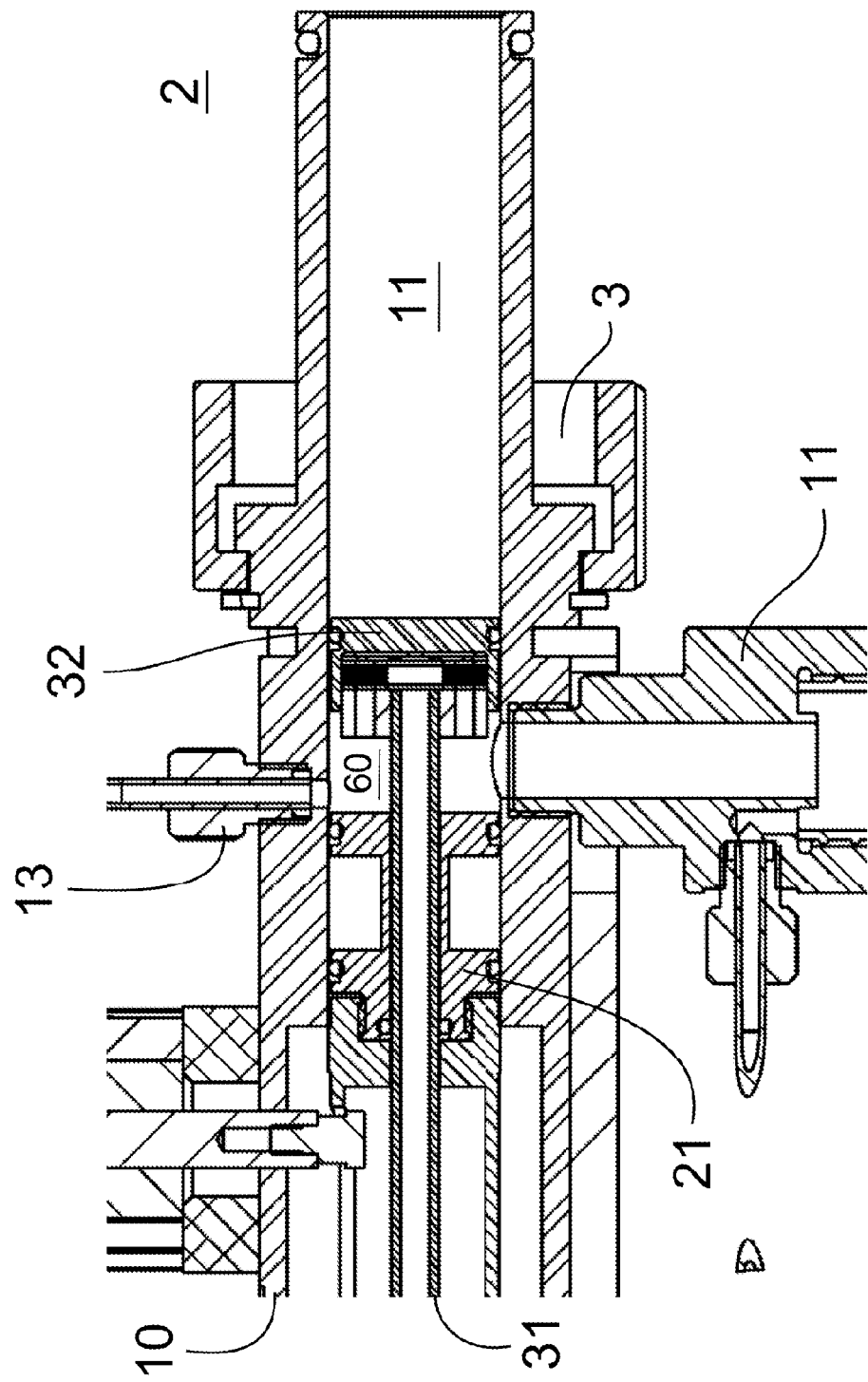
Figure 9:
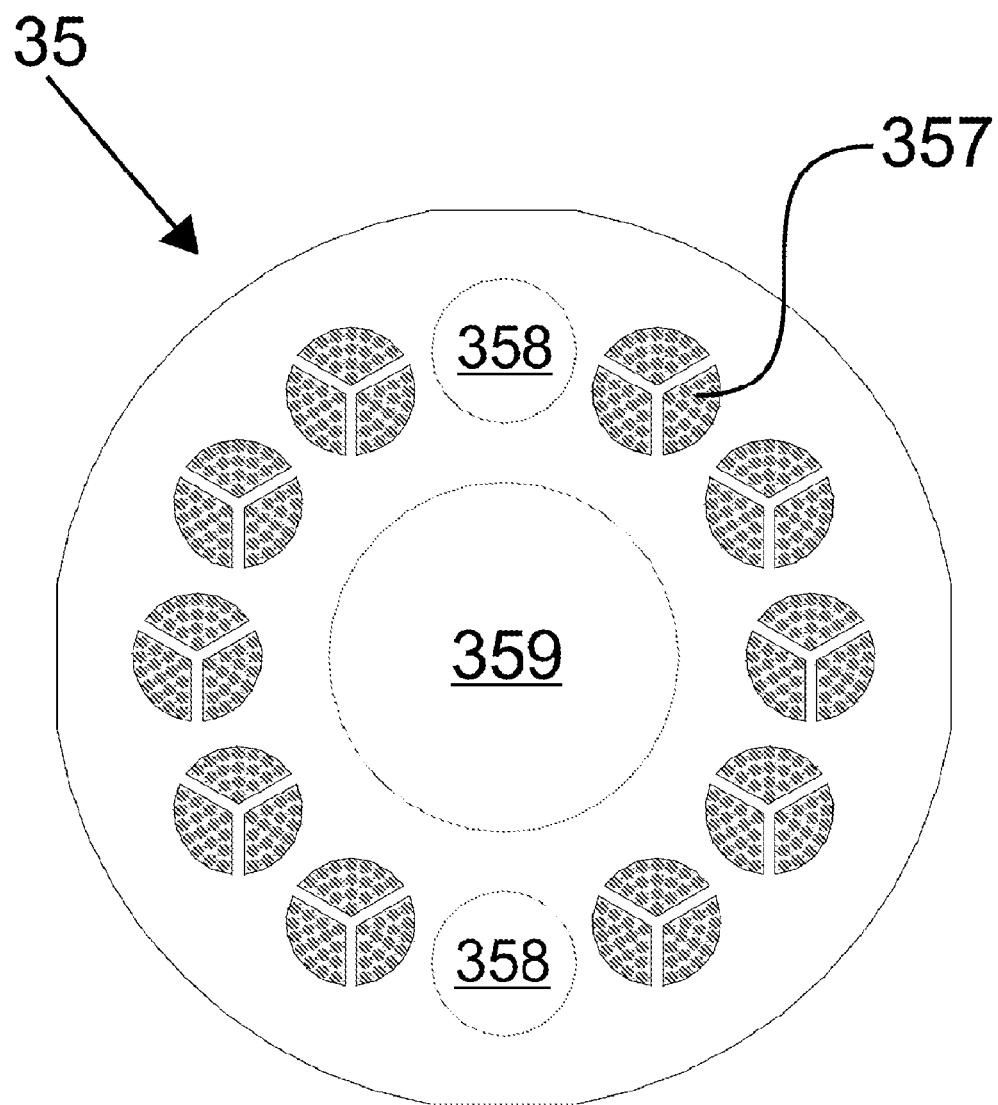
Figure 11:
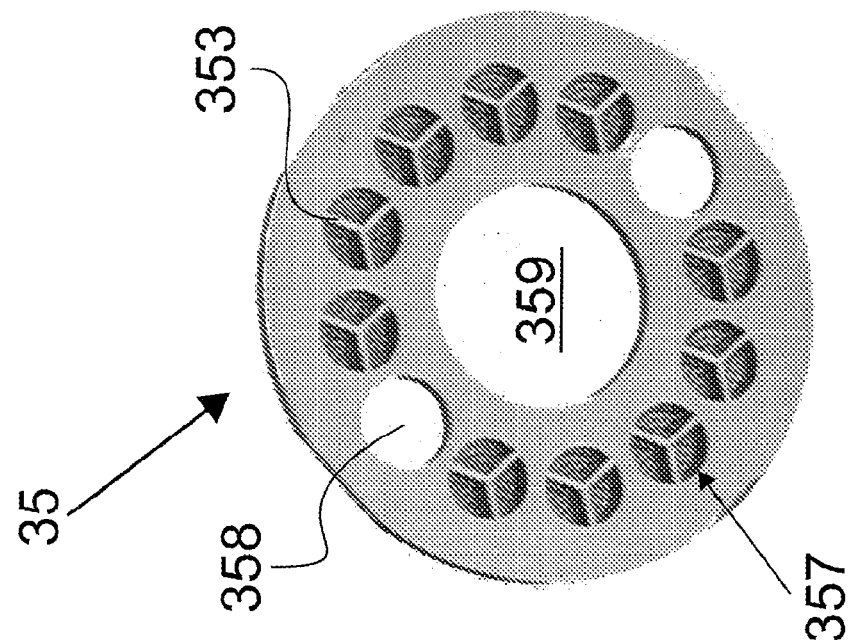
Figure 10:
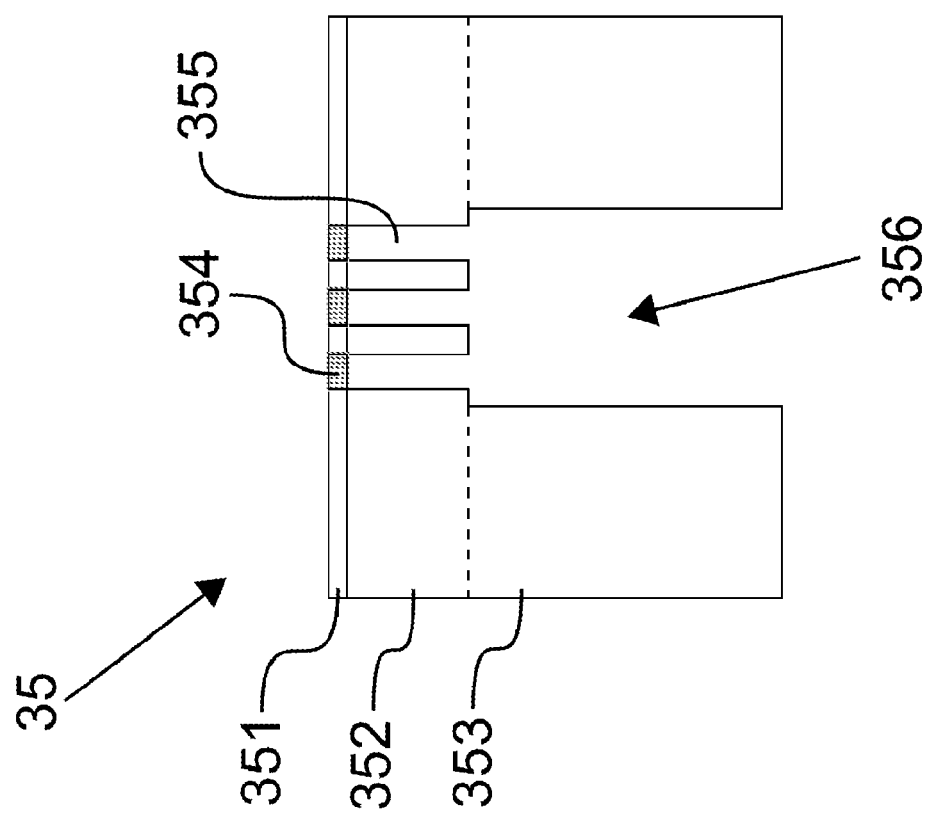
Figure 12:
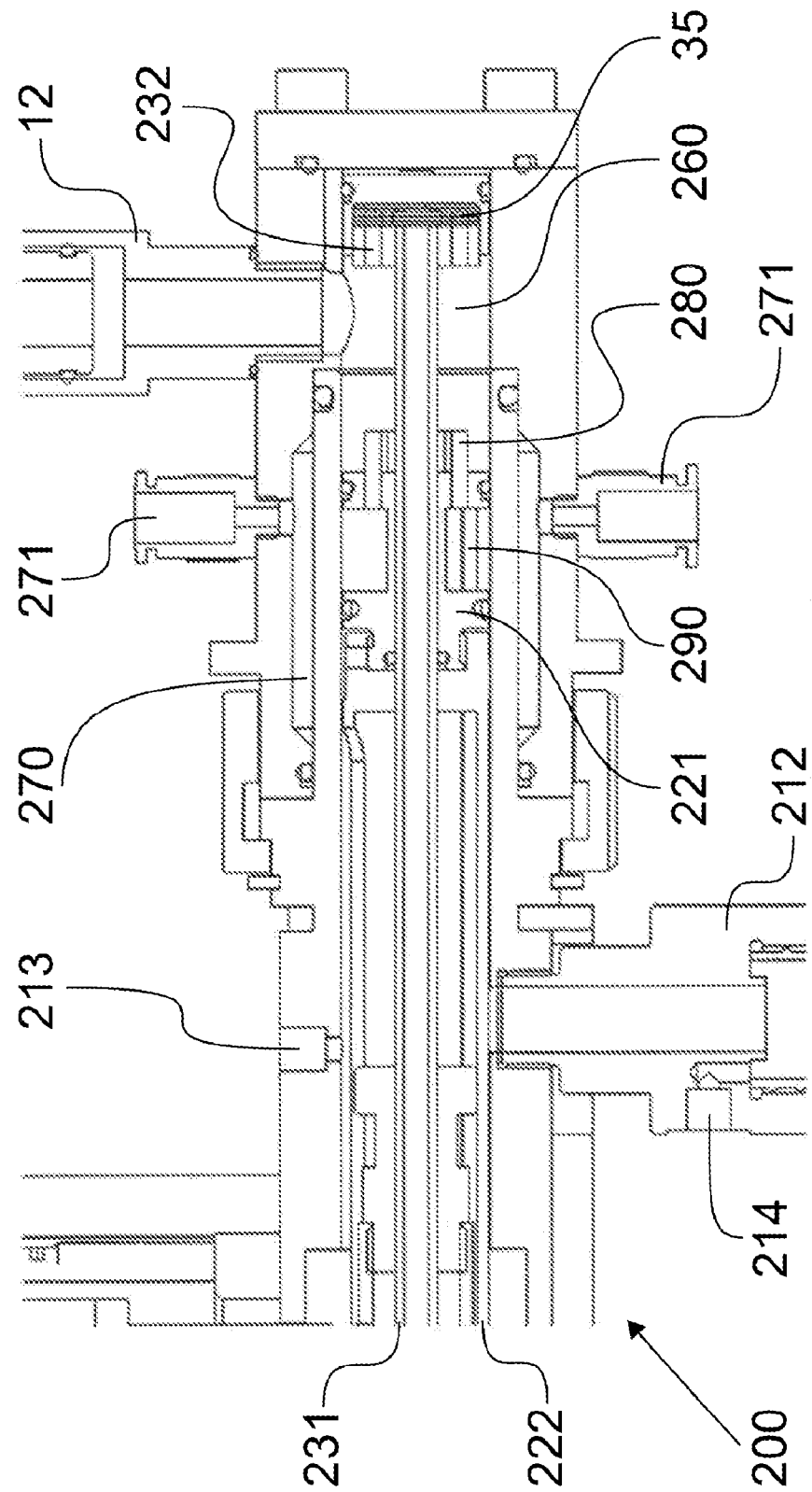
Figure 13:
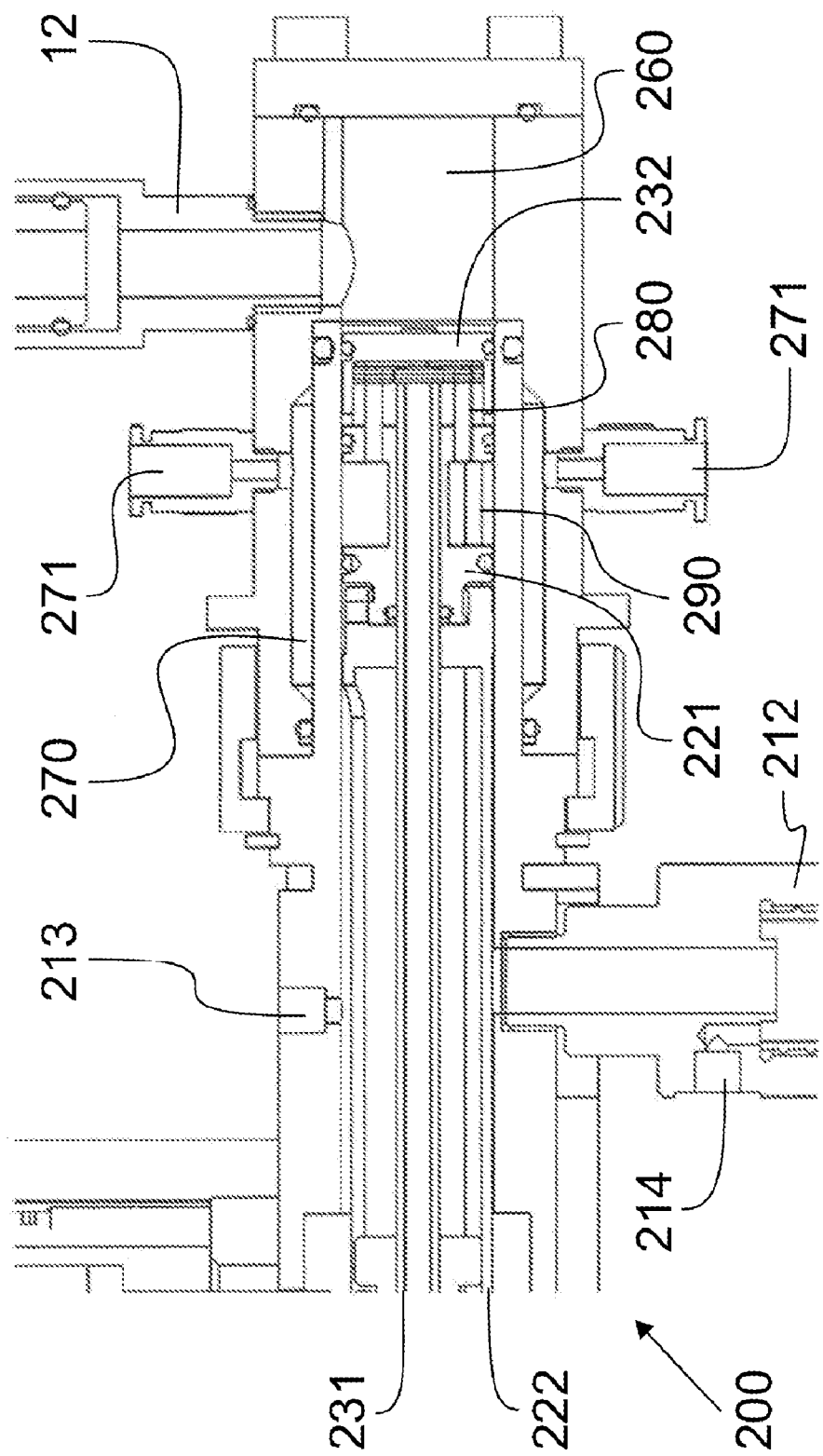
Figure 14:
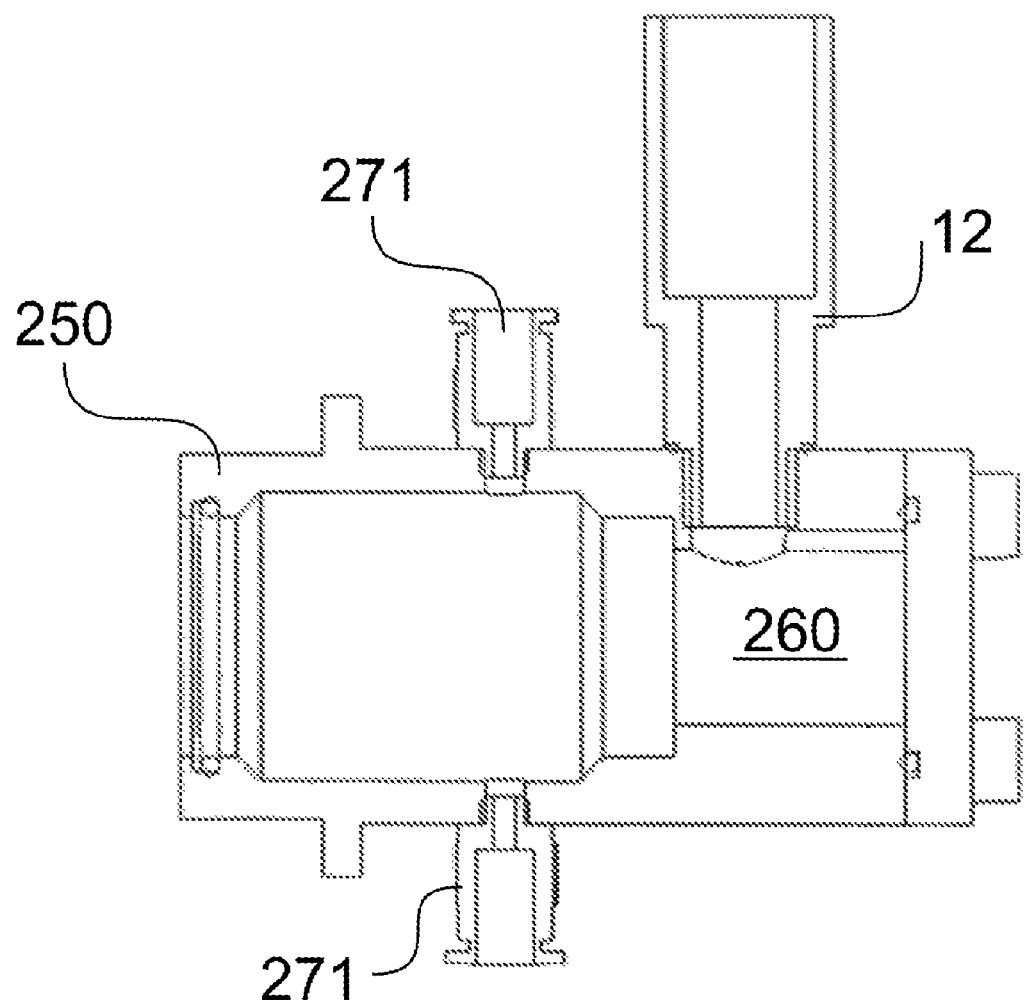
Figure 15:
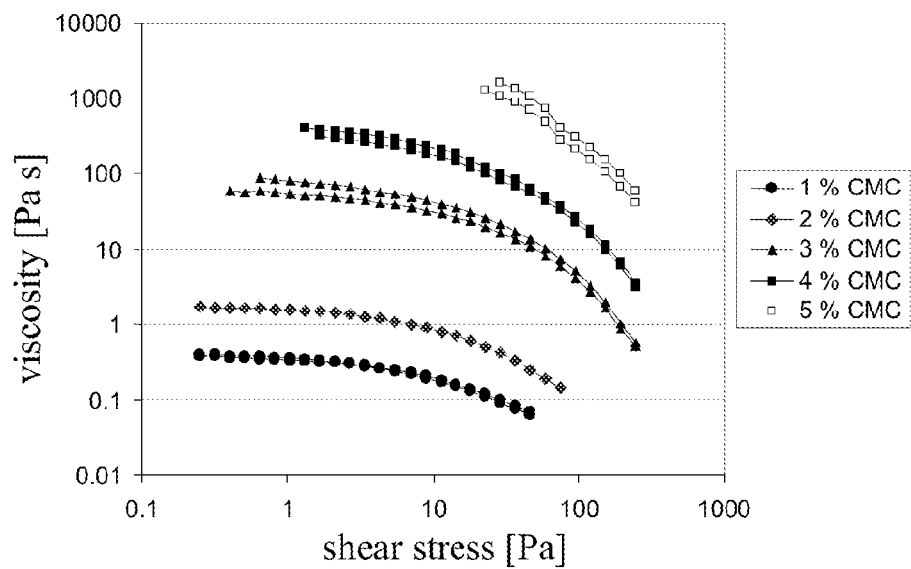
Figure 16:
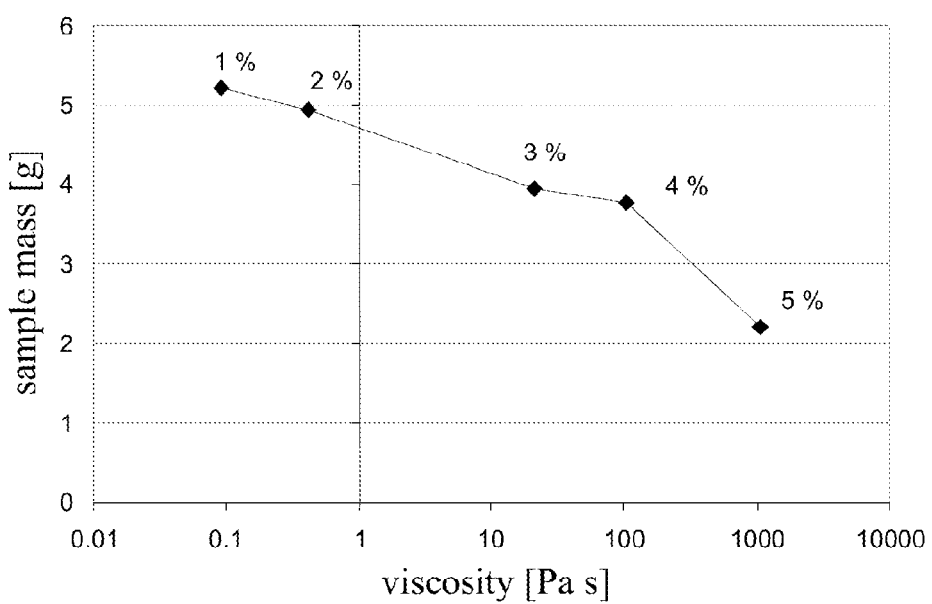

In the following, embodiments of the invention are examined with reference to the accompanying drawings, in which FIG. 1 shows the sample port according to the invention in the sampling position, FIG. 2 shows a cross-section of the body of the sample port, FIG. 3 shows a cross-section of the second plunger assembly, FIG. 4 shows the first plunger assembly, FIG. 5 shows a cross-section of the sample connection of the first plunger assembly, FIG. 6 shows a cross-section of the first plunger, FIG. 7 shows an exploded view of the first plunger, FIG. 8 shows the sample port in the compression position, FIG. 9 shows a filter for the plunger according to the invention, FIG. 10 shows across-section of the filter according to FIG. 9, FIG. 11 shows a perspective view of the filter according to FIG. 9, seen from in front in the filtering direction, FIG. 12 shows a cross-section of a sample port according to one embodiment of the invention, in the receiving position, which is connected to a second sample port according to the invention, FIG. 13 shows a cross-section of the sample port according to FIG. 12, which is in the processing position, FIG. 14 shows a cross-section of part of the body of the sample port according to FIGS. 12 and 13, FIG. 15 shows the viscosities, with the shear forces as the variable, of test samples taken using a sample ort according to the invention, and FIG. 16 shows how much sample of mixtures of different viscosities the sample port according to the invention can take.

As can be seen from FIG. 1, the sample port according to the invention comprises two consecutive plungers 21, 32 inside a cylindrical hollow body 10. The body 10 has a cylindrical internal cavity 11 (FIG. 2), the longitudinal axis of which, i.e. the direction parallel to the symmetry axis of the cross-section, will be referred to in this connection as the axial direction.

As can be seen from FIG. 2, the internal cavity 11 has two diameters of different sizes. In the rear portion of the body 10, in other words in the portion farthest from the sampling object such as a bioreactor 2, the diameter of the internal cavity 11 is larger than in the front portion of the body 10. In addition, the body 10 is equipped with an attachment ferrule 15, for attaching the sample port to the sampling object 2, which is typically a bioreactor or similar container, in which the substance, from which a sample is to be collected for study, is cultivated or grown. The reactor 2 is usually equipped with a sample-port connection (not shown), which is, for example, a tube facing outwards from the reactor 2 and equipped with an external thread. The sample port's attachment ferrule 15 is equipped with a corresponding internal thread, so that the sample port can be easily connected tightly to the reactor 2.

As can further be seen from FIG. 2, two channels lead to the internal cavity 11 of the sample-port body 10. The upper of these channels is a gas connection 13, through which a fluid substance, such as water vapour, can be led to the internal cavity 11, in order to sterilize the internal cavity 11, or to eject a collected sample into the lower channel. The lower channel is the sample-container connection 12, to which a container can be attached in order to receive a collected sample. According to one embodiment, the sample-container connection 12 too is equipped with its own gas connection 14, through which water vapour, for example, can be fed into the body 10, in order to clean the sample port in the opposite direction to that of the gas connection 13. The operation of the gas connections 13 and 14 is dealt with in greater detail later.

As stated, two plungers are arranged inside the body 10 of the sample port, of which the first plunger assembly 30 is shown in FIG. 4 and the second plunger assembly in FIG. 3. The second plunger assembly 20 comprises a plunger rod 22 and a plunger 21 attached to the front end of it. The second plunger assembly 20 is equipped with a centre hole to receive the first plunger assembly 30. The second plunger rod 22 is hollow and its rear end is equipped with a hole for the pin of the actuator moving the plunger. In this connection, the term front end refers to the sample port or part of it, which is closest to the reactor 2. Correspondingly, the term rear end refers to the sample port or part of it, which is farthest from the reactor 2. The jacket of the plunger 21 itself is equipped with a radial groove 24, into which, according to one embodiment, it is also possible to take a sample, as described in greater detail later. The outer edges of the flanges on both sides of the radial groove 24 are equipped with grooves, into which a sealing ring 23 is fitted, in order to seal the plunger 21 in the internal cavity 11 of the body 10. Thanks to the two sealing surfaces, the plunger 21 does not allow the sample to move unintentionally into the wrong places in the internal cavity 11.

The first plunger 32 is shown in greater detail in FIGS. 6 and 7, of which FIG. 6 shows that the first plunger rod 31 is hollow and that the plunger base 33 is attached to its front end. There is a centre hole in the plunger base 33, which is aligned with the internal cavity of the plunger rod 31. FIG. 6 also shows that there are threaded holes in the plunger base 33, to take screws 51, which screws 51 secure the outer plunger 38 to the plunger base 33. The outer plunger 38 is cylindrical in shape, so that its jacket protects the components inside the first plunger 32.

The first plunger 32 is shown in greater detail in FIG. 7, from which it can be seen that a filter 35, which is between two internal seals 34, is fitted between the plunger base 33 and the outer plunger 38. The purpose of the filter 35 is to filter a pressurized sample as a liquid for analysis. Conversely, the said filter 35 prevents the solid component of the sample from entering the liquid component of the sample. The plunger base 33 is equipped with through holes, which are parallel to the plunger rod 31, i.e. the holes are axial. The holes are intended to lead a sample to be compressed into the first plunger 32. Thus, according to the embodiment shown here, the holes in the plunger base 33 and the filter 35 form filter means for separating the liquid component of the pressurized sample from its solid component. Within the scope of the invention, the filtering means can also be implemented in a manner differing from that described above. This is because the filtering means can be correspondingly arranged in the second plunger 21, which, it is true, would make the construction more complex than that of the embodiment shown, due to the arrangement of the sample connection. Alternatively, the filtering means can also be fitted to the body 10, for example as part of the inner surface of the internal cavity 11, though in that case the manufacture of the body 10 and the sealing of the plungers 21, 32 will be challenging.

As stated, the jacket of the outer plunger 38 surrounds the filter 35 and the other internal components, so that a sample being compressed by the plunger 32 will not escape from the plunger 32 but will be led to the centre hole in the plunger base 33 and from there to the hollow plunger rod 31. There are also corresponding holes in the internal seals 34. In addition, there is an inner spacer 36 and sealing ring 37 fitted between the front internal seal 34 and the outer plunger 38. The inner spacer 36 is shaped to create a flow channel, which leads from the holes of the filter 35 to the centre hole of the hollow plunger rod 31 removing the sample. In addition, the outer plunger 38 is sealed to the inner surface of the internal cavity 11 on the body 10 by an O-ring 39, which is set in a corresponding groove in the outer jacket of the outer plunger 38.

The filter 35 is preferably a multi-stage, i.e. multi-layer filter plate made from silicon. As can be seen from FIGS. 9 and 11, according to one embodiment, the filter 35 according to the invention is a plate with a circular cross-section, which is equipped with a centre hole 359, which, in the assembly, is fitted in alignment with the centre hole of the first plunger rod 31, in order to lead the sample to the sample connection 40. In addition, in the plate there are two through holes 358 for the screws 51 of the first plunger 32. Ten identical filter elements 357, in each of which there are forty-eight filter membranes 351, are formed in the filter 35. A cross-sectional view of the filter 35 is shown in FIG. 10, from which it can be seen that the filter 35 is three-stage. The filter 35 comprises a support beam 353 and two consecutive membranes 352 and 351, which filter out particles of different sizes, according to the sizes of their holes. The three-branched full-height support beam 353 is equipped with a hole 356 with a diameter of 2.2 mm, which support beam 353 filters out particles larger than 1 mm. The height of the hole 356 is then about 525 µm. The following membrane 352, in the direction of filtering, which is about 100-µm thick, is equipped with holes 355 of a diameter of about 200 µm, which correspondingly filter out 200-1000-µm-sized particles. The final filtering is performed in the visible 10-µm thick membranes 351. Each membrane 351 contains about 4500 holes 354, the diameter of which corresponds to the filtering requirement, for example, 200 nm. The holes 354 thus filter out particles with a size of 0.22-200 µm. Filtering can also be performed in the opposite direction, in which case all particles larger than 0.22 µm will stop at the membrane 351, which is not advantageous in terms of flow.

The following describes an example of the dimensioning of a filter 35 according to the invention. The filter can be, for example, a silicon disc about 700-µm thick, with a diameter of about 15.5 mm. The disc comprises, as well as the centre hole 359 and the auxiliary holes 358, ten filter elements 357 with a diameter of 2.2 mm. Further, the 2.2-mm diameter filter element 357 is divided by a support beam 353 into three sectors, the thickness of the membranes 352 of which is about 100 µm. Each 200-µm-diameter hole 355 in the membrane 352 is equipped with a membrane 351, of which there are thus 480 in the entire filter 35. The diameter of the membrane 351 is thus 200 µm and contains a number of through holes 354, the size of which is determined by the current filtering requirement. According to one embodiment, the filter 35 is a sterile filter, due to which the diameter of the through holes 354 in the membrane 351 is 200 nm. Through holes 354 of other sizes are also practicable, but 200 nm is regarded as being the limit for sterile filtering. There will then be about 2.2-million through holes 354.

According to another embodiment, thin-film electrodes are integrated in the filter 35 according to FIGS. 9 and 10, for counting the particles that have passed through, using electrical detection.

According to yet another embodiment, the surfaces of the filter 35 according to FIGS. 9 and 10, which are in contact with the samples, are surfaced with a coating of titanium dioxide ($TiO_2$), which further improves the purifying effect of the filter 35. According to one embodiment, the filter 35 according this embodiment can be illuminated with UV light, which promotes the purification of the filter surface. Alternatively, the purification and selective passage of the filter 35 can be improved by means of coating increasing the hydrophilic or hydrophobic properties of the surface.

As stated, the filter 35 can also be implemented in other alternative ways. Instead of a silicon disc, in theory, the filter 35 could be manufactured from laser-machined steel, if such small holes could be created by laser machining that the passage of microbial cells could be prevented. Unlike the previous embodiment, the filter 35 of one embodiment is preferably a porous ceramic plate. The advantage of a ceramic filter 35 is its excellent wear-resistance properties, its ease of manufacture, and its price, but a drawback is the spongy and porous structure of ceramics, which easily becomes blocked and is difficult to flush, especially as counter flushing. According to another embodiment, the filter 35 is of a traditional membrane form, for example, a thin membrane made from Teflon, the structure of which is, like that of ceramics, spongy and porous, with the same blockage problems, but with poor durability.

The first plunger assembly thus comprises a first plunger rod 31 and a plunger 32 attached to the front end of it. In addition, the first plunger assembly comprises a sample connection 40, which is attached to the rear end of the assembly (FIG. 4). As can be seen from FIG. 5, the first plunger rod 31 is protected by a cover tube 44. An adapter ferrule 43 is attached by a thread to the rear end of the cover tube 44, and connects the cover tube 44 to the plunger rod 31, in such a way that it remains firmly in place. The second task of the rear-end adapter ferrule 43 is to connect a tube 41, in which the liquid component of the sample travelling along the plunger rod 31 is collected, to the rear end of the first plunger rod 31. The movement of the liquid sample component to the rear end of the tube 41 is ensured by introducing a pressurized substance, such as air, nitrogen gas, or water vapour, in the system from a gas connection 13 or a vacuum in the other end of the tube 41, or by using both methods. Thus, the hollow first plunger rod 31 and the sample connection 40 connected to it form the means according to the embodiment described for leading the liquid sample component away for the space between the plungers. Within the scope of the invention, the said means can also be implemented in a manner differing from that described. If, for example, the filter 35 is fitted to the second plunger 21, the means for leading the liquid sample component away from the space between the plungers must naturally be fitted in connection with the second plunger 21.

Thus, the tube 41 is attached to the plunger rod 31 by a connector 42, which is attached to the adapted ferrule 43 by a tight threaded joint. The sample connection 40 formed by the adapter ferrule 43, the connector 42, and the tube 41 can in turn be connected to a container or analyser suitable for the purpose, in which the collected liquid component of the sample can analysed. A corresponding adapter ferrule 43 without a connector adapter is also fitted between the cover tube 44 and the first plunger rod 31 at its front end (not shown).

In sampling, the first plunger 32 of the sample port is pushed into the reactor 2, as shown in FIG. 1. The distance between the first 32 and the second 21 plunger then determines how much sample is collected. Once a sufficient amount of sample has been obtained between the plungers 21, 32, the plungers 21, 32 are retracted into the internal cavity 11 of the body 10. As can be seen from FIG. 8, when the plungers 21, 32 are inside the body 10, a sample chamber 60, which is delimited by the internal surface of the internal cavity 11, remains between them. The size of the sample chamber 60 naturally depends on how far from each other the first 32 and the second 21 plungers are kept. In a case in which there are solids in the sample, the sample port according to the invention can be used so separate a liquid and solid component from the sample. In this connection, the term a high solids content refers to a situation, in which at most 90% of the substance is liquid. In other words, solids form at least 10% of the sample. The high solids content of a sample can also be examined through its flow properties, which determine inversely the viscosity.

The invention is also suitable for substances with a high viscosity, which can be in the order of 400 Pa·s, even up to 4000 Pa·s, i.e. more than one million cP, which roughly corresponds to the order of congealed molten glass. In order to illustrate a particular application, FIGS. 15 and 16 show details of the possible viscosity properties of substances processed using the sample port according to the invention. On the basis of tests performed, it has been ascertained that the sample port according to the invention is suitable for sampling a high-viscosity reaction mixture. The information is based on tests, in which the sample port according to the invention was tested by way of example using five different solutions of carboxymethylcellulose in water (1-5% CMC), from which samples with a volume of 5 ml were taken using the sample port. The viscosities of the samples taken were determined using a StressTech rheometer (Reologica Instruments Ab, Sweden), using various shear-force settings. The viscosities determined from the samples are shown in FIG. 15 as variables of the shear forces. By means of the sample port according to the invention, a sample can even be obtained from a mixture, the viscosity of which is as much as about 1000 Pa·s at a shear force of 30 Pa. Such a sample will remain in a test tube, even if the tube is inverted. For its part, FIG. 16 shows how much sample the sample port according to the invention can take from mixtures of different viscosities.

Thus, with the aid of the sample port according to the invention, samples can be taken, which will remain in a sample container that has been inverted. In order to separate the liquid and solid components of a sample with a high solids content, the first 32 and second 21 plungers are pressed against each other with such a force that the second plunger 21 compresses a pulpy sample in such a way that it penetrates from the axial hole of the plunger base 33 (FIG. 7) of the second plunger 32, towards the filter 35. When the pressure is sufficient, the liquid phase of the sample is filtered through the filter 35 and travels through the through hole of the plunger base 33 (FIG. 6), through the hollow first plunger rod 31 to the sample connection 40, and from there by means of the tube 41 to a container, or automatic analyser or similar.

Once the liquid component of the collected sample has been recovered, the solid component of the sample remains in the axial holes in the first plunger 32 and between the plungers 21, 32. In order to recover this solid component, the plungers 21, 32 are moved to the location of the sample-container connection 12 (FIG. 2). The dry sample being collected will then be above the sample-container connection 12, when the sample is ejected into the sample-container connection 12 by blowing it with gas flowing from the gas connection 13. The gas flow of the gas connection 13 pushes the dry component of the sample into the sample-container connection 12, from where it can be further led into a test tube 16 attached to the sample-container connection 12, or directly to an analyser for analysis. The test tube 16 can be a typical 5 or 50-milliliter threaded test tube, the material of which is plastic, for example. Test tubes of this type are available commercially. According to an alternative embodiment, the solid sample can also be collected, instead of in a test tube 16, in a second sample port, in which it is further processed.

If residues from the dry component of the sample have remained in the holes in the plunger base 33 of the first plunger 32, they can be removed by injecting compressed gas in the first plunger rod 31, for example, using gas led through a branched piece (not shown) attached to the tube 41. By thus flushing the plunger base 33 with counter-flow gas, i.e. counter flushing, all of the dry sample is recovered in the sample-container connection 12. Thus, at this stage, all of the sample taken is utilized precisely and no pieces of the old sample will remain in the components of the sample port, so that the old sample will no longer endanger the following sampling.

Once both the liquid and solid components of the sample have been collected, the sample port can be cleaned without having to detach it from the sampling object 2. This is because sterilizing gas can be led into the sample-container connection 12 through the gas connection 14, when the internal cavity 11 is cleaned. The filter 35 can be flushed, for example, in such a way that steam is led into it through the first plunger rod 31. The waste arising during flushing can be led into the sample-container connection 12, when the collected sample must be moved away from underneath, preferably for analysis. In cleaning the system, allowance must be made for the fact that, when taking a new sample, the gas used for emptying remains in the internal cavity 11 of the sample port, which gas will enter the reactor 2 during the new sampling. In this case, nitrogen gas, or some other gas that has no effect on the process, is used for emptying, especially in processes that must not come into contact with oxygen.

According to another embodiment, the filter 35 is utilized when separating the liquid sample component from the solid, in such a way that the first plunger 32 is pushed into the reactor, in which a sample with a high solids content is sucked through the filter 35. The vacuum required to suck the sample is created using a vacuum pump or similar (not shown) connected to the sample connection 40. From the sample connection 40, the liquid sample component is forwarded for analysis using the same vacuum or another pressure-difference arrangement, so that waste sample does not remain in the tubing, unlike in traditional in situ filtering methods. Once the liquid component has been recovered—again unlike the existing in situ filtering—the first plunger 32 is retracted into the reactor 2 and cleaned by flushing, as described above. When the first plunger 32 has been emptied into the reactor 2, the solid sample component, corresponding mainly to the liquid sample component, comes into contact with the substance from which the sample of the substance has been taken. In the long term, this distorts the ratio of the liquid to the solid sample component, due to which the in situ filtering according to this embodiment is not an optimal procedure.

In addition, by means of the sample port according to the invention, a sample can be collected, in such a way that a liquid and solid phase are not separated from the sample. According to one embodiment, in connection with sampling, the sample is not taken between the first 32 and second 21 plunger, as described above, but instead the second plunger 21 is moved so far into the sampling object 2 that the sample travels back into the internal cavity 11 in the radial groove 24 of the plunger 21. The first plunger 32 is then kept pressed against the second plunger 21, so that the sample will not remain between the plungers 21, 32. As above, the collected sample is transported to above the sample-container connection 12, where the sample is emptied, either with the aid of gravity, or assisted by compressed gas blown from the gas connection 13. The sample is thus collected as such, each time in an amount determined by the volume of the radial groove 24 of the second plunger 21. Flushing of the sample port is performed, as described above.

According to one embodiment, sample ports according to the invention are connected in series. According to one particular embodiment, they are connected in series, in such a way that the solid-sample sample-container connection 12 of the first sample port is connected to the sample chamber 260 of the second sample port 200, as shown in FIG. 12, in which the second sample port 200 is in the sample receiving position. The sample's solids separated by the first sample port can thus be further processed, i.e. they can be extracted in the sample chamber 260 of the second sample port 200, which acts as a reaction chamber. The second sample port 200 is arranged to filter the liquid fraction created in the extraction from the remaining solids. This allows a liquid extract to also be obtained from the solid sample component, which can be sent to an automatic analyser connected to the apparatus. Automatic measurement permits automatic control of the process. Thus, the second sample port 200 is arranged to further process the solid component of the collected sample, which increases the degree of automation of the sampling.

According to one embodiment, the solid sample sent to the second sample port 200 is chemically disintegrated, in order to promote analysis. Disintegration is performed by feeding into the sample chamber 260 from the gas connection 13 acting as a flushing channel a substance that deflocculates or otherwise disintegrates the substance, for example an acid such as sulphuric acid, or a solvent such as ethanol. The dispersing agent fed will naturally depend on the composition of the sample to be disintegrated. Chemical dispersion naturally required that the first and second plungers 232 and 221 have been moved against each other, so that the sample to be disintegrated is pressed between them and the sample to be disintegrated has been pushed to the location of the gas connection 13 supplying the dispersing agent. A separate gas connection (not shown) can also be arranged to supply the dispersing chemical agent, in which case the gas connection 13 will only be used for emptying or cleaning the sample chamber 260, or for both.

According to another embodiment, a solid sample delivered to the second port 200 is disintegrated thermally by increasing the temperature of the sample port 200 sufficiently, in which case the solid sample will disintegrate as a result of the increase. The sample port 200 is then moved to the processing position, in which the first 232 and second 221 plungers are moved towards each other, so that the sample to be disintegrated is between the plungers 232, 221, as shown in FIG. 13. Thermal disintegration can be implemented in several different ways. This is because the second sample port 200, more specifically its body, can be equipped with a thermal resistance, which is arranged to heat the sample chamber 260 (not shown). Alternatively, the second sample port 200 can be equipped with a separate heating channel 270, as shown in FIGS. 12-14. According to the embodiment shown in FIGS. 12-14, the heating channel 270 is a radial space, which is formed on the outer edge of the internal sample chamber 260 of the body 250. The heating channel 270 can be manufactured in numerous different ways, for example, by casting a cavity inside the body 250, but in the examples of FIGS. 12-14, the channel 270 is implemented by manufacturing the body 250 of the sample port 200 for two parts attached to each other, between which the heating channel 270 remains. In addition, the heating channel 270 is equipped with two fluid connectors 271, which are located on opposite sides of the sample chamber 260 and along which a warm or hot fluid, vapour, or gas is conducted to the heating channel 270.

If the sample must be cooled for disintegration, the cooling can be implemented using corresponding structures, in such a way that the thermal resistance is replaced with a Peltier element and the warm fluid led to the heating channel 270 is replaced with a cool or cold fluid.

According to yet another embodiment, a solid sample delivered to the second sample port 200 is disintegrated mechanically, in which case the plungers 221, 232 of the second sample port 200 can press against each other, in order to achieve mechanical disintegration. According to one embodiment, an element disintegrating the sample can than be fitted to the second sample port 200, which element can be, for example, a mat of needles 280 attached to the second plunger 221, when the sample will be compressed between the filter 35 and the needle mat 280, in order to disintegrate a solid sample (FIG. 12). In the case of a needle mat 280, its construction preferably the opposite of that of the filter 35 of the first plunger 221, so that in the needle mat 280 there are spikes corresponding to the positions of the holes. The needle mat 280 can be manufactured, for example, from silicon or stainless steel, which can be easily cleaned using the cleaning element, such as the gas connection 13, already in the sample port 200.

According to yet another embodiment, the disintegration of a solid sample delivered to the second sample port 200 is boosted by ultrasound, in which case the sample port, preferably its second plunger 221, will be equipped with an ultrasound head 290. The ancillary devices required by the ultrasound head 290, such as an ultrasound converter (not shown), are located on the outside of the sample port 200, from which the necessary signals are transmitted to the sample port 200 by vias and conductors. According to one embodiment, especially preferably the ultrasound head 290 is fitted behind the needle mat 280, which needle mat 280 will reinforce the mechanical abrasion.

The disintegration of the solid sample component preformed in the second sample port can also be implemented using some combination of the embodiments described above. Alternatively, the solids-processing means 270, 271, 280, 290 of the sample port 200 can also be fitted to the first sample port.

| Reference-number list | |
|---|---|
| No. | Part |
| 2 | sampling object |
| 3 | sample-port connection |
| 10 | body |
| 11 | internal cavity |
| 12 | sample-container connection |
| 13 | gas connection |
| 14 | gas connection |
| 15 | attachment ferrule |
| 16 | sample tube |
| 20 | second plunger assembly |
| 21 | second plunger |
| 22 | second plunger rod |
| 23 | sealing ring |
| 24 | radial groove |
| 30 | first plunger assembly |
| 31 | first plunger rod |
| 32 | first plunger |
| 33 | plunger base |
| 34 | internal seal |
| 35 | filter |
| 36 | internal spacer |
| 37 | sealing ring |
| 38 | outer plunger |
| 39 | O-ring |
| 40 | sample connection |
| 41 | tube |
| 42 | connector |
| 43 | adapter ferrule |
| 44 | cover tube |
| 51 | screw |
| 60 | sample chamber |
| 200 | second sample port |
| 210 | body |
| 212 | sample-container connection |
| 213 | gas connection |
| 214 | gas connection |
| 221 | second plunger |
| 222 | second plunger rod |
| 231 | first plunger rod |
| 232 | first plunger |
| 260 | sample chamber |
| 270 | heating channel |
| 271 | fluid connection |
| 280 | needle mat |
| 290 | ultrasound head |
| 351 | membrane |
| 352 | membrane |
| 353 | support beam |
| 354 | hole |
| 355 | hole |
| 356 | hole |
| 357 | filter element |
| 358 | through-hole |
| 359 | centre through-hole |

The invention claimed is:

1. Sample port, to be connected to a sample-port connection of a reactor or a bioreactor, the sample port comprising;
a body, which has an internal cavity with an internal surface;
two plungers, which are arranged in the body, in such a way that they can be pressed against each other in the internal cavity, in order to compress a sample, and at least one of which plungers is movable related to the body into the reactor for collecting the sample, at least one of the plungers being hollow;
a sample chamber which is delimited by the internal surface of the internal cavity;
at least one sample-container connection which is in connection with the internal cavity for collecting the sample from the sample chamber;
wherein the sample port further comprises:
filter means for separating a liquid component of the sample from a solid component, the filter means being attached to the at least one of the plungers such that the filter means is configured to lead the liquid component of the sample out of the sample chamber via the at least one of the plungers.

2. Sample port according to claim 1,
wherein the filter means comprises a filter for filtering out the solid component of the sample.

3. Sample port according to claim 2,
wherein the filter is attached to a first plunger of the two plungers.

4. Sample port according to claim 3,
wherein the first plunger comprises:
a plunger base, which is attached to a front end of the first plunger and which has axial holes for guiding the sample into the first plunger, and
an external plunger, which is attached to the plunger base, in such a way that a space for the filter remains between them.

5. Sample port according to claim 1,
wherein the sample port further comprises a hollow first plunger rod, to a free end of which a first plunger of the two plungers is attached, and that a plunger base of the first plunger comprises a centre through-hole, which is aligned with an internal cavity of the first plunger rod, wherein the filter means is located between the plunger base and the first plunger rod in order to lead the sample through the filter into the first plunger rod.

6. Sample port according to claim 1,
wherein the sample port further comprises a gas connection, which is arranged to deliver a fluid substance into the internal cavity of the body, in order to blow the solid component of the sample into the at least one sample-container connection.

7. Sample port according to claim 1, wherein a second plunger of the two plungers is movable within the internal cavity.

8. Sample port according to claim 1, wherein the at least one sample-container connection is equipped with a gas connection.

9. Sample port according to claim 1, wherein a first plunger rod is driven pneumatically or by a motor, so that a first plunger of the two plungers can be automated.

10. Sample port according to claim 1, wherein a second plunger rod is driven pneumatically or by a motor, so that a second plunger of the two plungers can be automated.

11. Sample port according to claim 1, wherein a heating channel for heating or cooling the sample chamber is arranged in connection with the sample chamber, so that the sample in the sample chamber can be disintegrated thermally.

12. Sample port according to claim 1, wherein the sample port comprises an ultrasound head, which is attached to either of the two plungers and arranged to bring the either of the two plungers into a vibrating state, so that a sample in the sample chamber can be disintegrated mechanically.

13. Sample port according to claim 1, wherein the sample port further comprises a needle mat, which is fitted to the other plunger of the two plungers, so that the sample in the sample chamber can be disintegrated mechanically when the two plungers are pressed against each other.

14. Sample port according to claim 1, wherein a group of sample ports are connected in series, in such a way that a sample-container connection of a first sample port is connected with a sample chamber of a second sample port.

15. Multi-layer filter in combination with the sample port according to claim 1, wherein the filter means comprises:
- a filter body, which is equipped with a through hole,
- a number of filter elements, which are fitted to the filter body around the through hole, and each of which comprises at least one filtering membrane, which is equipped with holes according to a specific filtering requirement, wherein the filter elements comprise support beams, which are arranged to support the membranes in a direction in which the sample is passed through the multi-layer filter.

16. Multi-layer filter in combination with the sample port according to claim 15, wherein the multi-layer filter comprises two consecutive membranes each forming a filter element, the holes of a first membrane of the two consecutive membranes in the direction in which the sample is passed through the multi-layer filter are larger than the holes of a second membrane of the two consecutive membranes.

17. Multi-layer filter in combination with the sample port according to claim 16, wherein a diameter of the holes of a membrane arranged last in the direction in which the sample is passed through the multi-layer filter is at most 200 nm, in which case the multi-layer filter is a sterile filter.

18. Multi-layer filter in combination with the sample port according to claim 15, wherein the multi-layer filter is of silicon.

19. Multi-layer filter in combination with the sample port according to claim 15, wherein the multi-layer filter is ceramic.

20. Sampling method, in which:
- a first plunger is pushed into a bioreactor;
- the first plunger is retracted into a hollow body of a sample port, in such a way that the first plunger pushes a sample in front of the first plunger;
- the sample is compressed between a second plunger and the first plunger;
- a liquid phase of the sample is filtered by pressing the sample through a filter which is attached to the first plunger and leading the liquid phase of the sample through a hollow rod of the first plunger into a sample connection; and
- a solid phase of the sample remaining between the first and second plunger is ejected into a sample-container connection.

21. Method according to claim 20, wherein a solid component of the sample is ejected into the sample-container connection by flushing a cavity formed by the hollow body of the sample port with gas led from a gas connection connected to the cavity.

22. Method according to claim 21, wherein the sample port is counter-flushed using the gas connection of the sample-container connection.

23. Method according to claim 20, wherein the sample port is cleaned through the rod of the first plunger, in such a way that a sterilizing gas is led into the sample port through the rod of the first plunger and then through the filter which is attached to the rod of the first plunger.

24. Method according to claim 23, wherein a cavity formed by the hollow body of the sample port is flushed by leading a gas into it from a gas connection.

25. Method according to claim 24, wherein, in the flushing, a gas that has no effect on a process taking place in a sampling object at the time is used.

26. Method according to claim 20, wherein the solid phase of the sample is ejected into the sample-container connection, which is connected to a sample chamber of another sample port having the same structure, in which the sample is further processed.

27. Method according to claim 20, wherein a substance or a solvent that deflocculates or otherwise disintegrates the solid component of the sample, is lead into a sample chamber from a gas connection.

28. Method according to claim 20, wherein a sample chamber is heated using a thermal resistance in order to disintegrate the solid component of the sample or to promote its disintegration.

29. Method according to claim 20, wherein the first and second plungers are pressed against each other in order to achieve mechanical disintegration of the solid phase portion of the sample separated as a result of the filtering action.

30. Method according to claim 29, wherein the sample is disintegrated by pressing the sample against a needle mat which is fitted to the second plunger.

31. Method according to claim 29, wherein the sample is disintegrated by focussing ultrasound vibration on the sample by means of an ultrasound head fitted to the second plunger.

* * * * *